United States Patent [19]

Lotze et al.

[11] Patent Number: 5,328,769

[45] Date of Patent: Jul. 12, 1994

[54] GOLD(I) MERCAPTOCARBOXYLIC ACID ESTERS, METHOD OF THEIR PREPARATION AND USE

[75] Inventors: Marion Lotze, Hammersbach; Hans Mehner, Frankfurt, both of Fed. Rep. of Germany

[73] Assignee: Degussa Aktiengesellschaft, Frankfurt, Fed. Rep. of Germany

[21] Appl. No.: 63,773

[22] Filed: May 20, 1993

Related U.S. Application Data

[62] Division of Ser. No. 807,210, Dec. 16, 1991, Pat. No. 5,235,079.

[30] Foreign Application Priority Data

Dec. 18, 1990 [DE] Fed. Rep. of Germany ....... 4040446

[51] Int. Cl.$^5$ .................. B32B 15/00; B32B 17/06
[52] U.S. Cl. .................. 428/434; 427/126.1; 427/282; 427/421; 427/429; 428/446; 428/689
[58] Field of Search .......... 427/96, 126.1, 282, 427/421, 429; 556/113, 115, 117; 428/434, 446, 689

[56] References Cited

U.S. PATENT DOCUMENTS 4,221,826 9/1980 Baltrushaitis et al. ............... 427/96

FOREIGN PATENT DOCUMENTS 1298828 3/1959 Fed. Rep. of Germany .
1284808 4/1963 Fed. Rep. of Germany .

Primary Examiner—Michael Lusignan
Attorney, Agent, or Firm—Beveridge, DeGrandi, Weilacher & Young

[57] ABSTRACT

Novel gold(I) mercaptocarboxylic acid esters of the formula (I)

$$Au-S-X-\underset{\underset{O}{\|}}{C}-O-Z$$

in which X is a $C_1$- to $C_3$ alkylene group and Z is a group from the series tricyclo(5,2,1,0$^{2.6}$)decane-8- or -9-yl or tricyclo (5,2,1,0$^{2.6}$)decyl-3- or -4-methyl. These esters can be prepared from mercaptocarboxylic acid esters of the formula (II)

$$HS-X-\underset{\underset{O}{\|}}{C}-O-Z$$

and from a gold(I) chloride-dialkylsulfide complex. The novel esters can be used in gold preparations for gilding solid bases, especially ceramic materials. Compared to known gold(I) mercaptocarboxylic acid esters, the novel esters result in considerably shorter drying times for gold preparations.

17 Claims, No Drawings

GOLD(I) MERCAPTOCARBOXYLIC ACID ESTERS, METHOD OF THEIR PREPARATION AND USE

This is a divisional of co-pending application Ser. No. 07/807,210 filed on Dec. 16, 1991, now U.S. Pat. No. 5,235,079, patented Aug. 10, 1993.

BACKGROUND TO THE INVENTION

The present invention relates to novel gold(I) mercaptocarboxylic acid esters which are characterized by a tricycloalkyl group in the alcohol component of the ester. The present invention also concerns a method of preparing these new gold mercaptides and their use in gold preparations for gilding solid bases.

So-called gold preparations have long been used to apply a gold decoration onto ceramic articles and to produce strip conductors of gold in integrated circuits. Such preparations generally contain one or several sulfur-organic gold compounds soluble in an organic carrier medium, fluxing agents such as e.g. resinates of one or several of the elements B, Si, V, Cr, In, Sn, Sb, Bi, and Rh, and the carrier medium contains a resin and organic solvent. The gold preparations are applied onto the surface to be coated and after the evaporation of the solvent, a burning process follows at a temperature adjusted to the substrate and the gold preparation, during which the gold film is formed and fixed with good adhesion to the surface.

The sulfur-organic gold compounds have long been almost exclusively so-called gold sulforesinates which were obtained from a gold salt and sulfurized terpenes, especially naturally occurring terpenes. One disadvantage of these sulforesinates is that their preparation is associated with naturally occurring raw materials whose supply is limited and whose quality is subject to variations. In order to eliminate these disadvantages, and at the same time influence the properties of the gold preparations in a purposeful manner, purely synthetically prepared gold(I) mercaptides with very different structures have been used in the gold preparations.

German patent 12 86 866 teaches defined, secondary gold(I) mercaptides with the formula RR'CH—S—Au in which R and R' signify alkyl, cycloalkyl, aryl or alkylaryl. The use of these gold(I) mercaptides required the use of strongly polar solvents such as nitrobenzene. Tertiary gold(I) mercaptides with the formula RR'R''C—S—Au with R, R' and R'' equal to alkyl are soluble according to DE-AS 12 98 828 in slightly polar solvents (e.g., toluene); in addition, these mercaptides exhibit lower decomposition temperatures. Finally, aromatic gold(I) mercaptides with the formula Ar—S—Au have also been suggested for gilding preparations (German patent 12 84 808). A bicyclic mercaptide, namely gold(I) bornyl mercaptide (U.S. Pat. No. 4,221,826), proved to be advantageous for the production of integrated electronic circuits. The above-named gold(I) mercaptides have the disadvantage of a partially very unpleasant odor which becomes particularly noticeable in a disturbing manner when the gold preparations are applied by heat (e.g., by means of hot screen printing).

DE-AS 12 92 463 teaches argentiferous (i.e., silver containing) gilding preparations containing a coordination compound consisting of a gold(I) mercaptide and an equimolar amount of a silver carboxylate or silver mercaptide. Primary or secondary alkyl- or alkylaryl-mercaptides and also gold(I) mercaptides of 2-methoxyethyl-, ethyl-, isooctyl- and tert.-dodecylthioglycolate are described as the gold(I) mercaptide. These coordination compounds are distinguished by greater solubility and better coating power in comparison to the individual compounds. The coordination compounds have the disadvantage that silver compounds are obligatorily present in equimolar amount and the creation of the decoration is thus limited in regard to the color. Moreover, the decorations are very susceptible to tarnishing phenomena due to the high silver content.

The family of gold(I) thioglycolic acid esters has a considerably more pleasant odor than the above-mentioned gold(I) mercaptides free of carboxyl groups.

Of the gold(I) thioglycolic acid esters cited in DE-AS 12 92 463, only gold(I) isooctylthioglycolate and gold(I) tert.-dodecylthioglycolate are basically suitable (in the absence of a stoichiometric amount of a silver compound) for use in gilding preparations in which a gold compound soluble in organic solvents is required (e.g., in bright gold preparations). Gold(I) ethylthioglycolate and gold(I)-2-methoxyethylthioglycolate are compounds which are almost insoluble in organic solvents.

However, as Applicants determined, the previously named isooctyl- and tert.-dodecyl-gold(I) thioglycolates are not satisfactorily suitable in gilding preparations, especially for the decoration of ceramic materials, because the drying time of the preparations is very long. This has a very negative influence on the economy of the decoration.

SUMMARY OF THE INVENTION

An object of the present invention is the development of gold(I) mercaptides which have less odor than the customary mercaptides without ester function and, in addition, a lower solvent retention in gold preparations of a customary composition, thus resulting in a shorter drying time than is the case with known thioglycolates.

According to the present invention, this and other objects are achieved by means of gold(I) mercaptocarboxylic acid esters of the formula

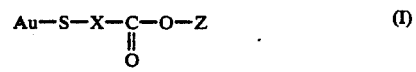

in which X represents an alkylene group and Z an alkyl group in which X is a $C_1$- to $C_3$ alkylene group and Z is a group from the series tricyclo(5,2,1,0$^{2,6}$) decane-8- or -9-yl or tricyclo (5,2,1,0$^{2,6}$)decyl-3- or -4-methyl.

DETAILED DESCRIPTION OF THE INVENTION

The novel gold(I) mercaptides of the present invention are derivatives of mercaptoacetic acid, 2- and 3-mercaptopropionic acid, 2-, 3- or 4-mercaptobutyric acid, and 2- or 3-mercaptoisobutyric acid. On account of their ready availability, products based oil mercaptoacetic acid (also called thioglycolic acid) and 2- or 3-mercaptopropionic acid are preferred.

The alcohol component of the ester, which component forms the base of the gold(I) mercaptides of the present invention, can exhibit one of the following structures:

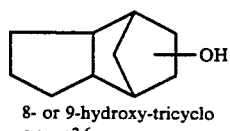

8- or 9-hydroxy-tricyclo
5,2,1,0²·⁶)decane or

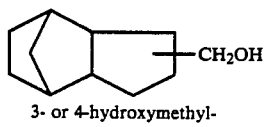

3- or 4-hydroxymethyl-
tricyclo-(5,2,1,0²·⁶)decane.

Naturally, these alcohols can be present in the form of one of the possible stereoisomers. However, mixtures of isomers (positional and/or stereoisomers) can be conveniently used for preparing the gold(I) mercaptides of the present invention and the novel substances are also accordingly usually mixtures of isomers.

Especially preferred gold(I) mercaptides in accordance with the present invention are gold(I) mercaptoacetic acid (tricyclo(5,2,1,0²·⁶)decyl-8 or -9) ester, gold(I) mercaptoacetic acid-( (tricyclo(5,2,1,0²·⁶)-decyl)-3- or 4-methyl) ester, gold(I) 2- or 3-mercaptopropionic acid-(tricyclo(5,2,1,0²·⁶)decyl-8 or -9) ester, and gold(I) 2- or 3-mercaptopropionic acid-(tricyclo(5,2,1,0²·⁶)decyl-3- or 4-methyl) ester. The novel substances can be identified by means of their chemical analysis and their melting point. The substances dissolve in the customary solvents (e.g., aromatic hydrocarbons) which are used in carrier media for gilding preparations.

The novel gold(I) mercaptides have broadened the palette of gold compounds which are particularly well suited for use in gold preparations. The special advantage of these novel gold(I) mercaptides is the fact that the drying time is shortened to a fraction of the drying time necessary for the closest previously known gold(I) mercaptoacetic acid esters. This shortening of the drying time, which can amount in individual instances to 90% or more, was unexpected and not foreseeable. These novel gold(I) mercaptides have only a slight odor and thus pose no problems as regards the work environment. It is possible to modify the properties of the gold(I) mercaptides by means of the selection and of the possibility of combining the X and Z groups and thus to adapt them more precisely to the desired use. Such an adaptation was not possible in the case of the gold(I) bornyl mercaptides of U.S. Pat. No. 4,221,826.

The novel gold(I) mercaptides of formula I can be prepared in a known manner like that known for the preparation of previously known gold(I) mercaptides (U.S. Pat. No. 4,221,826; DE-AS 12 86 866; DE-AS 12 98 828). A gold(I) chloride-dialkylsulfide complex, obtainable in a known manner by reacting an aqueous solution of tetrachloroauric acid with double the stoichiometric amount of a dialkylsulfide in the presence of water, is reacted with a mercaptocarboxylic acid ester of the formula

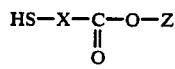  (II)

(in which X and Z have the same meaning as in formula I) in a molar ratio of about 1 to 1 in the presence of an organic solvent at 0° to 40° C. The organic solvent should dissolve the ester of formula II but practically not dissolve the desired gold(I) mercaptide of formula I. The expression "a molar ratio of about 1 to 1" means that a slight excess, up to 10 mole % of the ester of formula II, can be present; but a molar ratio of 1 to 1 is preferred. One of the previously known dialkylsulfide complexes, the dimethyl- or diethylsulfide complex, is a potential gold(I) chloride-dialkylsulfide complex which can be used as such or in the form of the reaction mixture obtained when preparing this complex; however, it is preferable if the gold(I) methionine complex is used. The gold(I) mercaptide of formula I precipitates during the reaction of the gold(I) chloride-dialkylsulfide complex with the ester of formula II. It is quite easy, when using methylene chloride as organic solvent, to obtain a powdery product which can be washed acid-free in a simple manner and which in particular does not contain any inclusions of the gold(I)-dialkylsulfide complex and mercaptocarboxylic acid ester used. The actual reaction is followed by solid-liquid phase separation, then a wash of the solid with water or aqueous solutions in order to remove the hydrogen chloride formed, and finally by drying. It is advantageous if residual water is removed before the drying by means of washing with a mixture of methanol or ethanol and methylene chloride or another low-boiling aliphatic chlorinated hydrocarbon. The drying preferably takes place at temperatures below 50° C.

The esters of formula II can be obtained by means of customary acid-catalyzed esterification methods from the mercaptocarboxylic acids and the tricyclic alcohols of the previously named structures in the presence of an azeotrope entraining agent. Toluene is an especially suitable entraining agent. A purification of the ester of formula II for preparing the gold(I) mercaptides of formula I is generally not necessary.

As has already been emphasized, the gold(I) mercaptocarboxylic acid esters of formula I can be used in gold preparations for gilding solid bases, especially those consisting of ceramic materials. The term "gold preparations" denotes liquid to pasty preparations which are applied according to various application methods (e.g., application by brush, spraying, indirect screen-printing (transfer pictures), or direct hot or cold screen-printing). The bases to be gilded must exhibit a sufficient thermal resistance in order to resist the burning process at which the gold film forms. The burning temperatures can be in a range of approximately 200° to over 1000° C., but in the case of ceramic surfaces temperatures in a range of 400° to 900° C. are preferred.

Gold preparations (compositions) for gilding ceramic materials (such as glass, glass ceramic, porcelain, and other silicatic or non-silicatic ceramic materials) also contain a fluxing agent and an organic carrier medium of resins and solvents in addition to the soluble gold compound. Moreover, other auxiliary processing substances as well as substances influencing the appearance and the properties of the gold film, such as other soluble noble-metal compounds, gold powder and glass frits, can be contained in the gold preparations. The gold content in the gold preparations suitable for decorative purposes as well as for technical purposes (such as printed circuits and lamp reflectors) can be within broad limits. So-called bright gold preparations usually contain 8 to 12% gold in the form of one or several gold(I) mercaptides; burnished gold preparations usually contain elementary gold in addition to the gold compounds (total gold content usually 15 to 40% by weight). Another class of gold preparations for which the gold(I) mercaptides of formula I can be used are the so-called gold luster preparations which contain only a low amount of gold (a few % by weight) but contain more gold fluxing agent along with the gold and do not comprise a cohesive gold film but rather a decoration with a characteristic golden luster.

The fluxing agents are like those initially cited and described in more detail in the documents cited above, that is, in particular, sulforesinates, resinares, naphthenates, carboxylates, and dithiocarbamates of the elements B, Si, V, Cr, In, Sn, Pb, Sb, Bi, and Rh. Typical carrier media contain one or several organic solvents from the series of ketones, aromatic and aliphatic hydrocarbons, aliphatic chlorinated hydrocarbons, alkyl acetates, glycol ethers, terpene hydrocarbons, and ethereal oils, as well as waxes in the case of media for hot screen-printing, and contain one or several resins from the series of wood resins (e.g., colophonium- and dammar resin) and synthetic resins (e.g., hydrocarbon resins, polyacrylates, and polymethacrylates). Typical bright gold preparations for screen-printing contain 20 to 30% by weight of the gold(I) mercaptides of the present invention, as pure compound or mixture of isomers, fluxing agent(s), especially mixtures of Cr-, Bi- and Rh resinates in an amount of 0.1 to 0.5% by weight calculated as chromium oxide, bismuth oxide and rhodium metal, and 65 to 80% by weight carrier medium (approximately a fourth of which is resins).

The drying speed of the gold preparation, under the same external conditions (temperature, pressure, and relative atmospheric humidity), is a function of the absolute evaporation speed of the solvent present, the extent of solvent retention by the organic components of the preparation, and also of the gold(I) mercaptide used. It turned out that, without adversely affecting the desired processing properties of a preparation, which are essentially determined by the type of carrier medium, the drying properties are influenced to an unexpectedly great extent by the structure of the organic gold compound. The structure of the substances of the present invention results in extraordinarily short drying times in comparison to previously known substances with a similar structure (see examples 3 and 4 and reference examples 1 and 2). The drying times are approximately the same within the group of the substances of formula I.

Determination of the drying time: Surfaces of 5×5 cm are printed with the gold preparation (screen-printing); the surface is coated with sea-shore sand at intervals of one half to one hour; the drying process is over when the sand falls off, due to insufficient adhesion, when the sanded surface is vertically positioned.

EXAMPLE 1

Preparation of the mercaptocarboxylic acid esters of formula II

Reaction of mercaptoacetic acid with 3(4)-hydroxymethyl-tricyclo(5,2,1,0$^{2.6}$)decane:

1.2 moles 98% mercaptoacetic acid (112.7 g) and 1 mole 3(4)-hydroxymethyl-tricyclo(5,2,1,0$^{2.6}$)decane (166.0 g) (isomeric mixture "TCD-Alkohol M" by Hoechst) dissolved in 250 ml toluene are heated in the presence of 2 g p-toluene sulfonic acid on a water separator under reflux (approximately 120° C.). After approximately 2.5 h, the theoretical amount of water (18 ml) has been separated. After having cooled off, the reaction mixture is neutralized, for the separation of the excess mercaptoacetic acid, with 10% by weight sodium hydroxide solution (approximately 80 ml) under agitation (approximately 30 min.). The aqueous phase is separated and the toluene distilled off under reduced pressure (15 mbars, 40° to 120° C.). 247.5 g of a colorless liquid with a residual toluene content of 3% by weight remain. The reaction takes place quantitatively. The raw mercaptoacetic acid-(tricyclo(5,2,1,0$^{2.6}$)decyl)-3(4)methyl)ester is reacted further without further purification.

Identification: $^1$H—NMR spectra.

Further products of formula II were prepared in basically the same manner using the particular mercaptocarboxylic acid and the above-named "TCD-Alkohol M" or 8(9)-hydroxytricyclo(5,2,1,0$^{2.6}$)decane (isomeric mixture "TCD-Alkohol A" by Hoechst).

EXAMPLE 2 a) Preparation of gold mercaptoacetic acid-(tricyclo)5,2,1,0$^{2.6}$)decyl-3(4)methyl)-ester 1 mole gold in the form of an aqueous solution of tetrachloroauric acid (38% by weight Au) (518.5 g) is added drop by drop within one hour into a suspension of 2 moles D,L methionine (298.4 g) and 2 liters water. The temperature is maintained at 0° to 5° C. by external cooling. After the end of the reduction, the gold(I) chloride-D,L-methionine hydrochloride complex is present partially in a dissolved form and partially as precipitate. 1 mole of mercaptoacetic acid-(tricyclo(5,2,1,0$^{2.6}$)decyl)-3(4)-methyl)-ester (240.1 g) mixed with 250 ml dichloromethane and 250 ml ethanol is added drop by drop at a temperature of 5° to 15° C. within one hour to this suspension. Gold mercaptoacetic acid-(tricyclo(5,2,1,0$^{2.6}$)decyl-3(4)-methyl)-ester accumulates as white precipitate which is filtered off immediately after the drop-by-drop addition. The precipitate is agitated for purification for 30 min. in 0.8 liter dichloromethane, compounded with 1.5 liters ethanol, agitated for 15 min. and removed by suction. The raw product is then agitated 30 min. with 450 g 3% sodium hydrogen carbonate, removed by suction and washed on a filter with 500 ml water. The raw product is agitated again 30 min. in 0.8 liter dichloromethane, compounded with 1.5 liters ethanol, agitated 15 min. and removed by suction. The raw product is dried in thin layers at 50° C. for 24 hours. The yield is about 98% relative to gold used.

Melting point: 172° C.

| Analysis: | Au | C | H | S |
|---|---|---|---|---|
| calc.: | 45.14 | 35.79 | 4.39 | 7.35 |
| obs.: | 44.92 | 35.68 | 4.32 | 7.30 |

The following gold mercaptides were prepared in a manner analogous to that described in example 2 from the corresponding mercaptocarboxylic acid esters:

b) Au—S—CH(CH$_3$)—COO—CH$_2$— 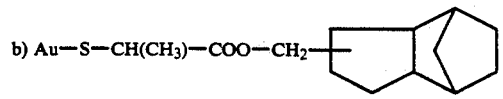

| | -continued | | | |
|---|---|---|---|---|
| Melting point: | 108° C. | | | |
| Analysis: | Au | C | H | S |
| calc.: | 43.74 | 37.34 | 4.70 | 7.12 |
| obs.: | 43.68 | 37.40 | 4.68 | 7.11 |

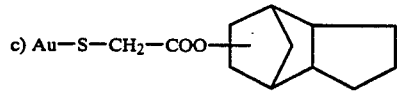

c) Au—S—CH$_2$—COO—

Au (theoretical): 46.64%
Au (experimental): 46.48%
Melting point: 138° C.

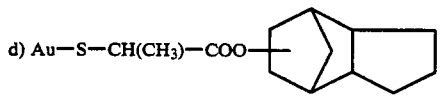

d) Au—S—CH(CH$_3$)—COO—

Au (theoretical): 45.14%
Au (experimental): 44.91%
Melting point: 97° C.

EXAMPLE 3 AND REFERENCE EXAMPLE 1

Bright gold preparations (according to the present invention and to the state of the art)—composition (data in % by weight) and drying times (hours)

| A | 54.13 | 24.39 | gold mercaptoacetic acid-(2-ethylhexyl)-ester in |
| --- | --- | --- | --- |
| | | 29.74 | mesitylene |
| B | 54.13 | 26.55 | gold mercaptoacetic acid(tricyclo (5,2,1,0$^{2.6}$)decyl-3(4)-methyl- |
| | | 27.58 | mesitylene |
| C | | 1.00 | rhodium sulforesinate in terpeniol, 5% Rh |
| | | 1.00 | bismuth resinate in terpeniol, 7% Bi$_2$O$_3$ |
| | | 1.50 | chromium resinate in terpeniol, 3% Cr$_2$O$_3$ |
| | | 20.00 | sulfurized colophonium resin |
| | | 22.37 | mesitylene |

The mixtures of A plus C (reference example 1) and B plus C (example 3) were applied onto glass plates by screen-printing (polyester screen fabric "110 T" 110 threads per cm., medium heavy).

The drying took place at 20° C. and a relative atmospheric humidity of 60%.

The bright gold paste consisting of components A and C required a drying time of 26 hours.

The bright gold paste consisting of components B and C (in accordance with the present invention) required a drying time of only 2 hours.

EXAMPLE 4 AND REFERENCE EXAMPLE 2

Bright palladium preparations (in accordance with the present invention and the state of the art)—composition (% by weight) and drying times (hours)

| A | 50.32 | 20.32 | gold mercaptoacetic acid-(2-ethylhexyl)-ester in |
| --- | --- | --- | --- |
| | | 30.00 | mesitylene |
| B | 50.32 | 21.44 | 2-gold mercaptopropionic acid-tricyclo(5,2,1,0$^{2.6}$)decyl)-8(9))-ester in |
| | | 28.88 | mesitylene |
| C | | 1.00 | rhodium sulforesinate in terpeniol, 5% Rh |
| | | 1.00 | bismuth resinate in terpeniol, 7% Bi$_2$O$_3$ |
| | | 1.50 | chromium resinate in terpeniol, 3% Cr$_2$O$_3$ |
| | | 6.30 | palladium sulforesinate in terpeniol, 8% Pd |
| | | 5.00 | silver sulforesinate, 20% Ag |
| | | 17.00 | sulfurized colophonium resin |
| | | 17.88 | mesitylene |

The mixtures of components A plus C (reference example 2) and B plus C (example 4) were applied in accordance with example 3/reference example 1 by screen-printing and the drying time determined.

Reference example 2: Drying time 18 h

Example 4: Drying time 1 h

Further variations and modifications of the invention will become apparent to those skilled in the art from the foregoing and are intended to be encompassed by the claims appended hereto.

German Priority Application P 40 40 446.3, filed on Dec. 18, 1990, is relied on and incorporated by reference in its entirety.

What is claimed:

1. A method of gilding solid bases, comprising applying a gold preparation comprising at least one gold (I) mercaptocarboxylic acid ester onto said solid base, wherein said gold (I) mercaptocarboxylic acid ester has the formula

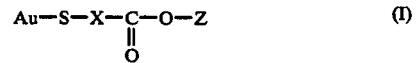

$$\text{Au}-\text{S}-\text{X}-\underset{\underset{\text{O}}{\|}}{\text{C}}-\text{O}-\text{Z} \quad \text{(I)}$$

in which X is an alkylene group and Z an alkyl group, wherein X is a C$_1$- to C$_3$ alkylene group and Z is selected from the group consisting of tricyclo(5,2,1,0$^{2.6}$)-decane-8- or -9-yl and tricyclo(5,2,1,0$^{2.6}$)decyl-3- or -4-methyl.

2. The method according to claim 1, wherein the thermal resistance of said base is about 200° to above 1000° C.

3. The method according to claim 2, wherein said base is ceramic material and said thermal resistance is 400° to 900° C.

4. The method according to claim 1, wherein said gold preparation further comprises a fluxing agent and an organic carrier medium comprising resins and solvents.

5. The method according to claim 4, wherein said gold preparation comprises 8 to 12% of said ester.

6. The method according to claim 4, wherein said gold preparation further comprises elementary gold and the total gold content in said gold preparation is 15 to 40% by weight.

7. The method according to claim 4, wherein said fluxing agent is selected from the group consisting of sulforesinates, resinates, naphthenates, carboxylates and dithiocarbamates of the elements B, Si, V, Cr, In, Sn, Pb, Sb, Bi and Rh.

8. The method according to claim 4, wherein said carrier medium comprises at least one organic solvent selected from the group consisting of ketones, aromatic and aliphatic hydrocarbons, aliphatic chlorinated hydrocarbons, alkyl acetates, glycol ethers, terpene hydrocarbons, ethereal oils, and waxes.

9. The method according to claim 4, wherein said carrier medium comprises at least one resin selected from the group consisting of wood resins and synthetic resins.

10. The method according to claim 9, wherein said wood resin is colophonium- or dammar resin.

11. The method according to claim 9, wherein said synthetic resin is selected from the group consisting of hydrocarbon resins, polyacrylates and polymethacrylates.

12. The method according to claim 4, wherein said gold preparation comprises 20 to 30% by weight of said ester, 0.1 to 0.5% by weight of a mixture of Cr-, Bi- and Rh resinates, and 65 to 80% by wight of said carrier medium.

13. The method according to claim 1, wherein said application is selected from the group consisting of brushing, spraying, and screen-printing.

14. A solid base gilded by the method according to claim 1, wherein said solid base is a ceramic material.

15. The solid base according to claim 14, wherein said ceramic material is selected from the group consisting of glass, glass ceramic, porcelain, silicatic ceramic material, and non-silicatic ceramic material.

16. The method according to claim 1, wherein X in said gold(I) mercaptocarboxylic acid ester is $CH_2$ or $CH(CH_3)$.

17. The method according to claim 1, wherein said gold(I) mercaptocarboxylic acid ester is selected from the group consisting of gold(I) mercaptoacetic acid (tricyclo$(5,2,1,0^{2.6})$decyl-8 or -9) ester, gold(I) mercaptoacetic acid-((tricyclo$(5,2,1,0^{2.6})$-decyl)-3- or 4-methyl) ester, gold(I) 2- or 3-mercaptopropionic acid-(tricyclo$(5,2,1,0^{2.6})$decyl-8 or -9) ester, and gold(I) 2- or 3-mercaptopropionic acid-(tricyclo$(5,2,1,0^{2.6})$decyl-3- or 4-methyl) ester.

* * * * *